(12) United States Patent
Huang et al.

(10) Patent No.: US 7,997,728 B2
(45) Date of Patent: Aug. 16, 2011

(54) MAPPING AND DIAGNOSIS OF MACULAR EDEMA BY OPTICAL COHERENCE TOMOGRAPHY

(75) Inventors: David Huang, South Pasadena, CA (US); SriniVas R. Sadda, Pasadena, CA (US); Ou Tan, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 855 days.

(21) Appl. No.: 11/743,135

(22) Filed: May 1, 2007

(65) Prior Publication Data

US 2007/0287932 A1 Dec. 13, 2007

Related U.S. Application Data

(60) Provisional application No. 60/796,811, filed on May 1, 2006.

(51) Int. Cl.
*A61B 3/00* (2006.01)
*A61B 13/00* (2006.01)
(52) U.S. Cl. .......................... 351/200; 351/246; 600/558
(58) Field of Classification Search ................ 351/200, 351/221, 246; 600/558
See application file for complete search history.

(56) References Cited

U.S. PATENT DOCUMENTS 6,267,477 B1 * 7/2001 Karpol et al. ................. 351/221
* cited by examiner

*Primary Examiner* — Jack Dinh
(74) *Attorney, Agent, or Firm* — DLA Piper LLP (US)

(57) ABSTRACT

The present invention discloses a method for comparing the detection of clinically significant diabetic macular edema by an optical coherence tomography (OCT) grid scanning protocol and biomicroscopic examination. Also provided are computer implemented, automated systems for performing the method thereof and computer readable media encoding the method thereof.

9 Claims, 10 Drawing Sheets

MAPPING AND DIAGNOSIS OF MACULAR EDEMA BY OPTICAL COHERENCE TOMOGRAPHY

CROSS-REFERENCE TO RELATED APPLICATIONS

This application claims an invention which was disclosed in Provisional Application No. 60/796,811, filed on May 1, 2006. The benefit under 35 USC §119 (e) of the U.S. provisional application is hereby claimed. The above priority application is hereby incorporated herein by reference.

STATEMENT REGARDING FEDERALLY SPONSORED RESEARCH AND DEVELOPMENT

The present invention is made, at least in part, with the support of NIH grant R01 EY013516. The government has certain rights in the invention.

FIELD OF THE INVENTION

The invention pertains to the field of ophthalmology. More particularly, the invention pertains to mapping and diagnosing macular edema by optical coherence tomography.

BACKGROUND OF THE INVENTION

Macular edema is an important cause of visual loss and legal blindness in patients with diabetic retinopathy. In the Early Treatment Diabetic Retinopathy Study (ETDRS) [1], focal laser photocoagulation was demonstrated to reduce the risk of moderate vision loss in diabetic patients with an entity termed clinically significant macular edema (CSME). As optical coherence tomography (OCT) was not available at the time of the EDTRS study, CSME was defined based on biomicroscopic observations by the examining physician. Three definitions of CSME were adopted by the ETDRS investigators: (1) presence of any retinal thickening within 500 µm of the foveal center, (2) lipid exudates within 500 µm of the foveal center with adjacent thickening, and (3) an area of thickening >1 Macular Photocoagulation Study disc area (DA; 1 DA≅1.767 mm$^2$) within 1 disk diameter (1.5 mm) of the foveal center. To corroborate and standardize the clinical assessment, the ETDRS Fundus Photographic Reading Center reviewed color stereoscopic photographs for a number of imaging end points, including the presence and extent of macular edema. Because accurate methods of quantifying axial retinal thickening were not available at that time, macular edema extent, as determined by biomicroscopic examination or inspection of stereoscopic photographs, was based only on the area of thickening and not on the magnitude of the axial thickness. Variations in the amount of stereopsis present in paired stereo photographs or in the threshold for thickening adopted by the observer may further complicate the accurate and reproducible detection of areas of edema. Thus, there is potential for considerable variability and possible lack of sensitivity in prior art methods for identifying macular edema that were used in previous clinical studies.

Furthermore, the lack of sensitivity of the clinical examination for detection of mild edema has been demonstrated by a number of investigators, including Brown et al. [2], who observed that, for eyes with a foveal center thickness between 201 and 300 µm (200 defined as the upper limit of normal), only 14% were noted to have foveal edema by contact lens biomicroscopy. They coined the term subclinical foveal edema to describe such cases. However, as these cases of subclinical edema were presumably not recognized in the ETDRS, the rationale for treating these lesions is presently uncertain, although it may change as data from ongoing clinical trials incorporating OCT imaging become available.

Although the system proposed by Brown et al. is useful for identification of foveal edema, it is not likely to identify cases of nonfoveal CSME. As OCT has become an integral part of clinical trials and clinical practice, a system for detection of nonfoveal CSME would be valuable. Unfortunately, the commonly used macular scanning patterns on the Stratus OCT machine (Carl Zeiss Meditec, Inc., Dublin, Calif.) consist of radial lines that provide a high density of points near the fovea, but a relatively sparse pattern in more peripheral zones. This requires considerable interpolation to construct a thickness map.

Therefore, there still exists a need for better methods to identify macular edema.

SUMMARY OF THE INVENTION

Accordingly, one object of the present invention is to provide better methods and tools for the detection and diagnosis of macular edema.

In one aspect, the present invention provides a method for analyzing a retinal thickness map of a subject comprising the step of comparing the subject retinal thickness map with a normal reference map to identify regions of abnormal retinal thickness in the macular region.

In another aspect, the present invention also provides a computer implemented system for identifying regions of macular edema in a subject. The system comprises an input for receiving source data from a retinal thickness map generating device, and a processing unit configured to perform a method according to embodiments of the present invention.

In yet another aspect, the present invention also provides a computer readable medium encoding instructions for performing an image analysis method according to embodiments of the present invention.

In still another aspect, the present invention provide a method for screening a population for retinopathy by analyzing the retinal thickness maps of individuals in the population using methods and systems according to embodiments of the present invention.

Other aspects and advantages of the invention will be apparent from the following description and the appended claims.

DETAILED DESCRIPTION

The present invention will now be described in detail by referring to specific embodiments as illustrated in the accompanying figures.

In one aspect, the present invention provides a method for analyzing a retinal thickness map of a subject to identify areas of abnormal thickness in the macular region.

In general, methods according to embodiments of the present invention comprises the steps of comparing the subject retinal thickness map with a normal reference map to identify regions of abnormal retinal thickness in the macular region, wherein the normal reference map is compiled from retinal thickness maps of a population with normal eyes, and wherein a point on the subject's retinal thickness map is abnormal if it meets predetermined comparison criteria.

Figure 1:
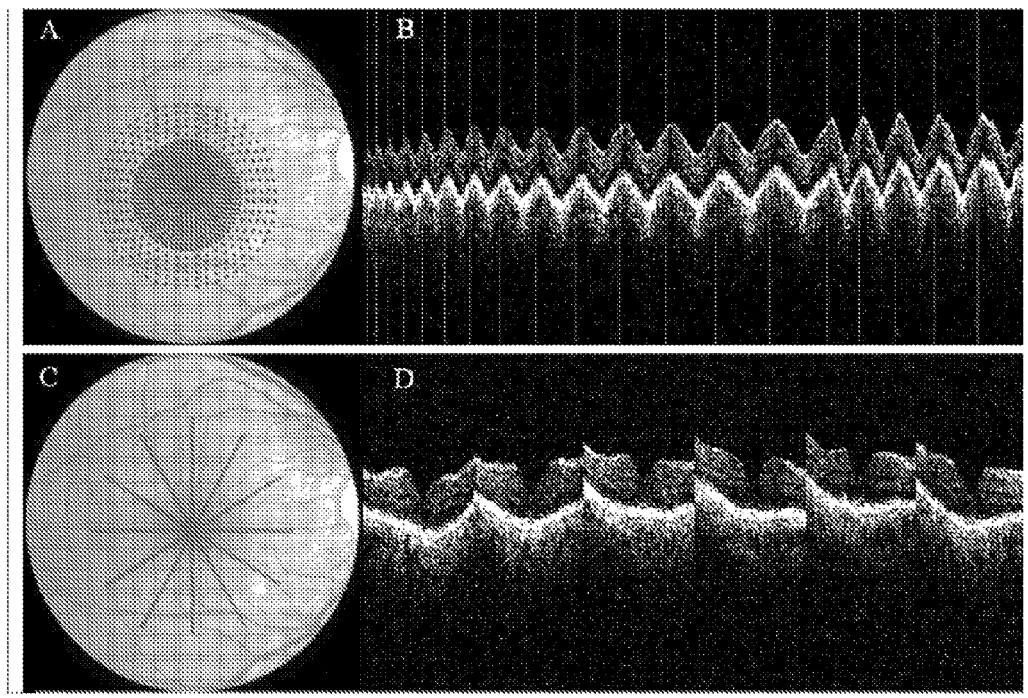
FIG. 1 (A) shows a Macular grid 5 (MG5) scan pattern; (B) shows an optical coherence tomography (OCT) image of MG5; (C) shows a Fast Macular Thickness Map scan pattern; (D) shows six OCT images corresponding to each of the 6 lines.

The retinal thickness maps may be generated from any suitable measuring devices. Exemplary retinal thickness map generating devices may include, but not limited to a slit scan retinal thickness analyzer, or any other retinal thickness analyzers commonly known in the art. In one embodiment, retinal thickness maps are preferably generated from optical coherence tomograms (OCT). In a further embodiment, the OCT preferably employees a scanning pattern that samples the macular region with relatively high uniformity. Exemplary scanning patterns may include, but are not limited to MG5 pattern as shown in FIG. 1. Other known scanning patterns or future envisioned scanning patterns may also be advantageously employed as long as the scan area is of suitable size. Preferably, the scan area is about 5 mm in diameter or larger. Scan area of about 7 mm in diameter is also known to produce excellent results.

Reference retinal thickness maps may be obtained by averaging retinal thickness maps of a population of healthy individuals with normal eyes. An exemplary reference retinal thickness map may contain average thickness values of each coordinate on the map and the corresponding standard deviations. The specific representation and units of the reference retinal thickness map are not particularly limited. In some embodiments, the maps may be represented in a multidimensional matrix. In other embodiments, the map may be represented as a mathematical function. The reference map may also be a composite map comprising both a mean value map and a standard deviation map. Other relevant parameters and forms of map representation known in the art are also contemplated.

In a preferred embodiment, a reference map of the present invention generally may be compiled as follows:

Subjects are assigned to normal group if both eyes had intraocular pressure (IOP) of less than 21 mm Hg, a normal Humphrey SITA 24-2 visual field (VF) (defined as having a mean deviation and pattern standard deviation within 95% limits of the normal reference and a glaucoma hemifield test within 97% limits), a central corneal thickness greater than 500 µm, an open anterior chamber angle, a normal-appearing optic nerve head, and a normal nerve fiber layer and normal retina in macular region and if the participant did not have a history of chronic ocular or systemic corticosteroid use.

The step of comparing the retinal thickness map of a subject to a reference map comprises making a comparison of the thickness value at each corresponding coordinate of the maps. If the value of the subject's retinal thickness map exceeds the value of the reference map at the corresponding map coordinate by a preset multiple of standard deviation, an abnormal thickness is indicated and it is included in the "edema zone". Selection of this preset "cut-off" threshold depends on the desired confidence level. Preferably, the preset threshold is about 2.33 standard deviations and above (99 percentile). Other useful threshold values include 1.65 standard deviations (95 percentile) or any other values between 1.65 and 2.33 standard deviations.

In some embodiments, a method of the present invention further comprises a step of identifying an edema kernel by finding one or more points on the subject's retinal thickness map whose value is greater than a predetermined multiple of standard deviations above the mean value at the same location of the normal reference map. The cut-off threshold for identifying the edema kernel points is preferably 2.60 standard deviation and above (99.5 percentile). Other suitable kernel thresholds include 3.09 standard deviations (99.9 percentile) to 2.33 standard deviations (99 percentile). When an edema kernel is identified, a method of the present invention may further comprise searching and identifying an edema zone by assessing the thickness of points neighboring the edema kernel and adding the point to the zone if it has a thickness greater than a predetermined thickness. The threshold level for the edema zone should be lower than that for the kernel. The value of the predetermined threshold thickness for the edema zone may be similarly selected as above, depending on the desired confidence level.

Based on the identified edema zone, methods of the present invention may further make diagnosis of clinically significant macular edema (CSME) if the edema zone fits a predetermined set of criteria. The criteria preferably are consistent with the recommendations of the Early Treatment Diabetic Retinopathy Study:

[CSME criterium 1] Any retinal edema (area >0 $mm^2$) within 0.5 mm radius of foveal center, or

[CSME criterium 2] retinal edema >1 disc area (edema area >1.767 $mm^2$) within 1.5 mm of foveal center.

Other embodiment of the current invention may also use other suitable values of distance from foveal center and area. The criteria can also be adjusted according to future studies on the treatment of diabetic macular edema or other forms of macular edema.

In another aspect, the present invention provides a computer implemented system for identifying regions of macular edema in a subject. In general, a system of the present invention comprises an input for receiving source data from a retinal thickness map generating device, and a processing unit configured to perform a method according to embodiments of the present invention as described above. Implementation of the system is not particularly limited so long as the processing unit is capable of performing a method of the present invention. For example, in some embodiments, a system of the present invention may be assembled from off-the-shelf components. In other embodiments, it may be a custom designed, integral system. The input may be a communication channel to a retinal thickness analyzer, a hardware interface to an electronic network, or any other suitable data acquisition means known in the art.

The processing unit may be a dedicated hardware circuitry, a general purpose computing unit such as a PC, a workstation, or any other suitable processing unit known in the art.

Various software tools may be used to configure the processing unit. For example, the processing unit may be equipped with customized machine codes to perform methods of the present invention to achieve maximum speed. Other software tools that may be used include, but not limited to pre-packed software tools such as Matlab, or application software developed in programming languages such as C, C++, JAVA, or any other programming language commonly known in the art.

In another aspect, the present invention also provides an automated system for identifying areas of macular edema in an eye, comprising a tomography device for obtaining a tomogram of the eye; a processing unit capable analyzing the tomogram, wherein the processing unit is configured to perform an analysis method having the general steps of (i) receiving the tomogram; (ii) computing a retinal thickness map from the tomogram; and (iii) identifying in the macular region where the retina is abnormally thick by comparing the retinal thickness map with the mean and standard deviation of the retinal thickness in similar locations in a population of normal eyes.

In yet another aspect, the present invention also provides a computer readable medium encoding instructions for performing a method according to the various embodiments of the present invention. Suitable computer readable medium may include, but not limited to floppy disks, hard drives, DVD-ROM, CD-ROM, flash memory card, or any other computer readable medium commonly known in the art.

In still another aspect, the present invention provides a screening method for screening a population for retinopathy by analyzing the retinal thickness maps of individuals in the population using methods and systems according to embodiments of the present invention.

A person skilled in the relevant art will readily recognize that the various aspects of computerization and automation represent different exemplary implementations and utilizations of methods according to the present invention. In a clinical setting, automation and computerization of diagnosis methods and data analysis methods have many advantages. Automation of a diagnosis or analysis method minimizes human involvement, thereby, reduces the chance of human error. In a clinical setting, computerization also enhances data acquisition precision and quality from patient to patient, thereby, allowing a clinic to deliver a more uniform and higher standard of service. Given the exemplary embodiments described above, other implementations and modifications not explicitly described are also possible.

To further illustrate the present invention, the following specific examples are provided.

EXAMPLES

Materials and Methods

1. Data Collection and Study Population

We retrospectively reviewed the clinical and imaging records of 71 eyes of 40 patients referred to the Doheny Ocular Imaging Unit with a diagnosis of diabetic macular edema (DME) who underwent OCT imaging using both the MG5 scan pattern (FIG. 1) and Fast Macular Thickness Map (FMTM). Approval for the analysis of these records was obtained from the institutional review board of the University of Southern California. For all OCT imaging studies, the Stratus OCT system with version 4.0 software was used to acquire the scan of the macula. Fast Macular Thickness Map and MG5 data from 65 normal subjects recruited from the Doheny Eye Institute and the University of Pittsburgh Medical Center were used as the reference baseline. The normal subjects were recruited as part of the prospective Advanced Imaging for Glaucoma Study. The study was approved by the institutional review boards of the University of Southern California and the University of Pittsburgh School of Medicine, and all participants provided informed consent before participating in the study. All methods adhered to the Declaration of Helsinki for research involving human subjects.

2. Comparison of Scanning Patterns

Figure 2:
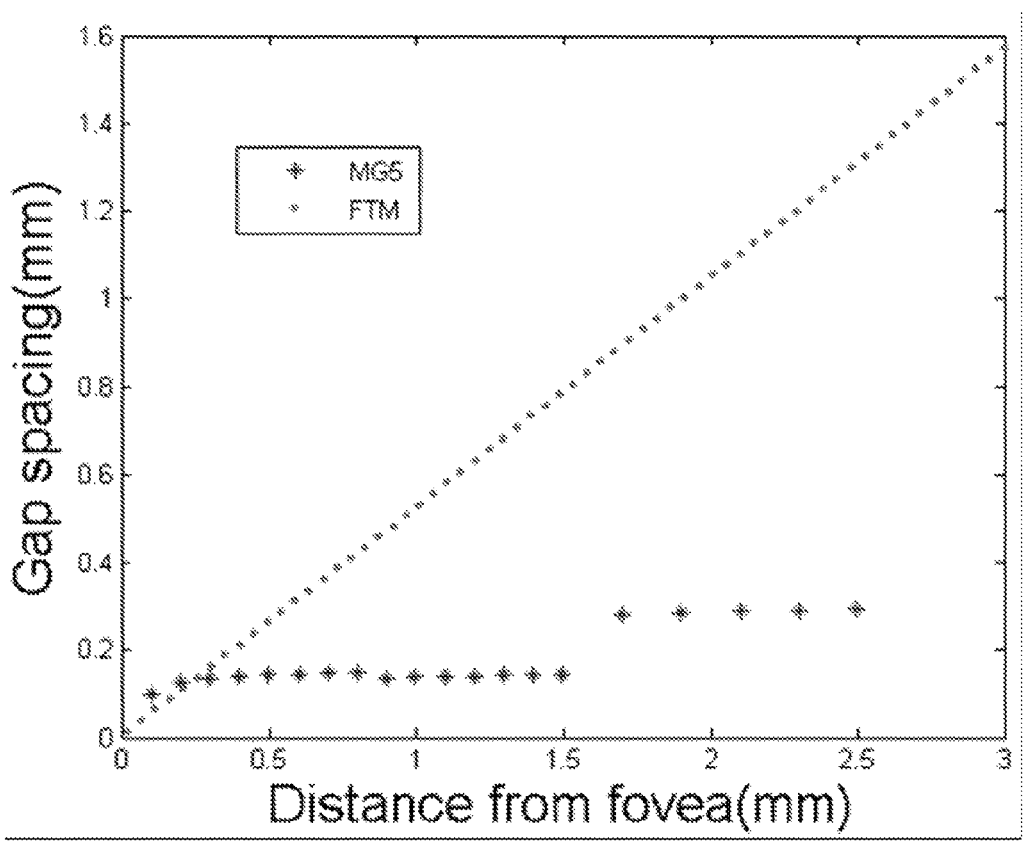
FIG. 2 shows a plot of gap between A-scan points plotted against distance from the center point (radius) for Fast Macular Thickness Map (FTM) scans and Macular Grid 5 (MG5) scans.

As illustrated in FIG. 1A, B, the MG5 scan algorithm obtains A-scans in a relatively evenly distributed pattern (MG5, 768 A-scans within the 5-mm-diameter grid), which minimizes unsampled gaps, particularly in the central 3 mm. In contrast, the standard Stratus FMTM (FIGS. 1C, D) leaves large gaps between the 6 scan meridians, with a progressive increase in the gap with increasing eccentricity, reaching a 1.3-mm gap at a distance of 2.5 mm from the center. FIG. 2 compares the meridian gaps of the 2 scan patterns. The MG5 scan was performed twice, thus allowing an assessment of the reproducibility of the scanning technique. The variation in measurements between scans was quantified using Bland-Altman21 95% limits of agreement analyses and plotted.

Figure 3:
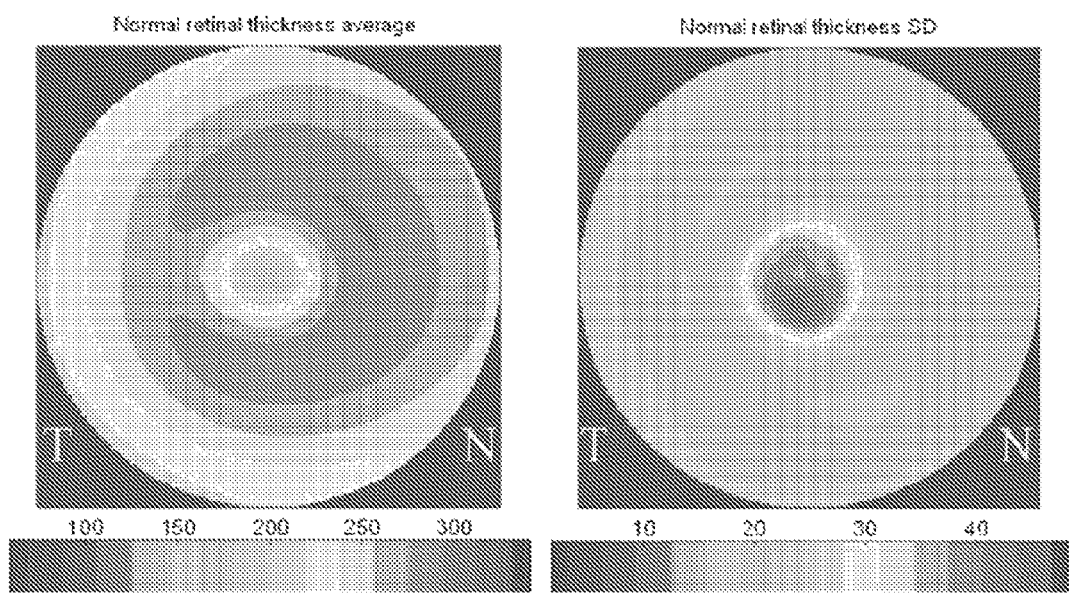
FIG. 3 shows the population average and standard deviation (SD) of retinal thickness map of normal reference. N=nasal; T=temporal.

3. Detection of Clinically Significant Macular Edema by Macular Grid 5 Optical Coherence Tomography To identify areas of potential retinal edema, the threshold for edema on the OCT map was defined arbitrarily as a retinal thickness >2.3 standard deviations (SDs) above the normal reference mean at that location (i.e., above the 99% level). The normal reference population consisted of 68 patients (56 of whom were women), with a mean age of 51±8 years. Of the 68 normal patients, 59 were Caucasian and 9 were African American; 17 patients identified themselves as being Hispanic. FIG. 3 shows the mean retinal thickness map and retinal thickness SD map of the normal reference population using the MG5 scanning pattern. An automated image processing algorithm for the MG5 scan data was developed to plot maps of retinal thickness, detect areas of edema, compute various parameters for the zones of retinal thickening (area, distance to fixation), and identify the presence of CSME. For identification of the retinal thickness, first the junction of the inner and outer segments of the photoreceptor is detected by the algorithm as the outer retinal boundary. A-scans with artifact or blocked reflectivity at the level of the retinal pigment epithelium are replaced with the results from neighboring A-scans. The inner nerve fiber layer boundary is then detected from the smoothed image as the inner retinal boundary. The distance from the inner to outer retinal boundaries is defined to be the retinal thickness. Finally, the retinal thickness map is interpolated between the sampled locations. The same method was applied to MG5 scans from the normal dataset to construct the normal reference map.

Points with a retinal thickness >2.6 SDs (99.5% level) above the normal reference mean at that location were identified as edema kernels. The edema kernel is the seed point from which surrounding points are then assessed to determine if thickening is also present. Regions were grown from the edema kernel to include contiguous surrounding points with thickness >2.3 SDs (99.0%) above the normal reference, to create zones of edema. The algorithm was designed, in accordance with ETDRS definitions, to identify 2 categories of CSME: CSME1, defined as retinal edema within 500 μm of the foveal center, and CSME2, defined as retinal edema >1 Macular Photocoagulation Study DA, of which at least some portion extended to within 1500 μm of the foveal center. For identification of CSME1, to reduce spurious detection of tiny islands of thickening caused by noise, a threshold area of thickening (0.2-mm diameter, 0.126-mm$^2$ area) was used to identify regions of true edema. The foveal zone (region affected by CSME1) is particularly susceptible to noise caused by motion artifact (due to poor fixation or transverse eye motion), given the significant normal difference in retinal thickness between the foveola and the parafoveal retina (FIG. 3). If any retinal edema was present (even if not CSME), a grade of DME was assigned. Using this nonexclusive scheme, it is important to note that a case of edema within 500 μm of the foveal center and with an area >1 Macular Photocoagulation Study DA would be classified as containing CSME1, CSME2, and DME. For the purposes of this analysis, the third ETDRS definition of CSME, the presence of lipid within 500 μm of the foveal center with adjacent thickening, was not identified due to difficulties of developing algorithms to identify lipid exudates accurately.

4. Clinical Diagnosis of Clinically Significant Macular Edema

The presence of CSME1 and CSME2, as identified by traditional methods of biomicroscopic examination and stereoscopic color photography, was determined by review of the clinical records. The macular drawings for each case were scrutinized first to determine if the edema was classified as CSME1 and/or CSME2 by the clinician. In cases in which the clinical record did not clearly categorize the CSME, stereoscopic color photographs obtained for the patient were reviewed by a trained member of the Doheny Image Reading Center (SRS) in an attempt to classify the edema. If macular edema was present, even when not deemed to be clinically significant, a grade of DME was assigned. In a few cases, although the patient was referred to the imaging unit with a diagnosis of macular edema, scrutiny of the clinical record did not identify any macular edema; these cases were assigned a grade of no DME. By this approach, an attempt was made to assign grades to every case. For the purpose of analysis, questionable grades were treated as if definitely present.

5. Stratus Optical Coherence Tomography Identification of Foveal Edema

To compare the performance of the MG5 algorithm with that of the manual interpretation of the standard FMTM algorithm for detection of CSME, an analysis was also performed of the retinal thickness maps generated by the Stratus OCT version 4.0 software. For this analysis, we adopted the criteria suggested by Brown et al [2] that foveal thickening <300 μm should be considered subclinical edema. Thus, foveal thickening <300 μm was deemed to meet the criteria for CSME1. Because CSME1 need not involve the foveal center, we chose to use the foveal subfield thickness (rather than the foveal center thickness) from the Stratus OCT output for the purpose of this analysis. In addition, because the identification of cysts (by biomicroscopy or by angiography) is frequently used by clinicians to identify the presence of thickening, we broadened the definition of CSME1 on FMTM to include cases in which retinal cysts were present in the fovea, even if the thickness was <300 μm. Attempts were not made to identify CSME2 from the FMTMs, given the large sampling gaps in the peripheral zones of this scan pattern.

6. Comparison of Methods for Grading Macular Edema

The MG5 assessments were compared with the clinical grade of the edema as determined by biomicroscopic examination and stereoscopic fundus photographs. The FMTM assessment for the presence of CSME1 was also compared with the clinical assessment. Sensitivities and specificities (assuming the clinical assessment to be the gold standard), K statistics (nonweighted, Cohen), [3] and agreement scores (defined as the number of cases for which the two methods agreed divided by the total number of cases) were calculated for all comparisons. K statistics were interpreted using the scheme advocated by Landis and Koch [4]: 0 to 0.20, slight agreement; 0.21 to 0.40, fair; 0.41 to 0.60, moderate; 0.61 to 0.80, substantial; and >0.80, almost perfect agreement.

Results

Figure 4:
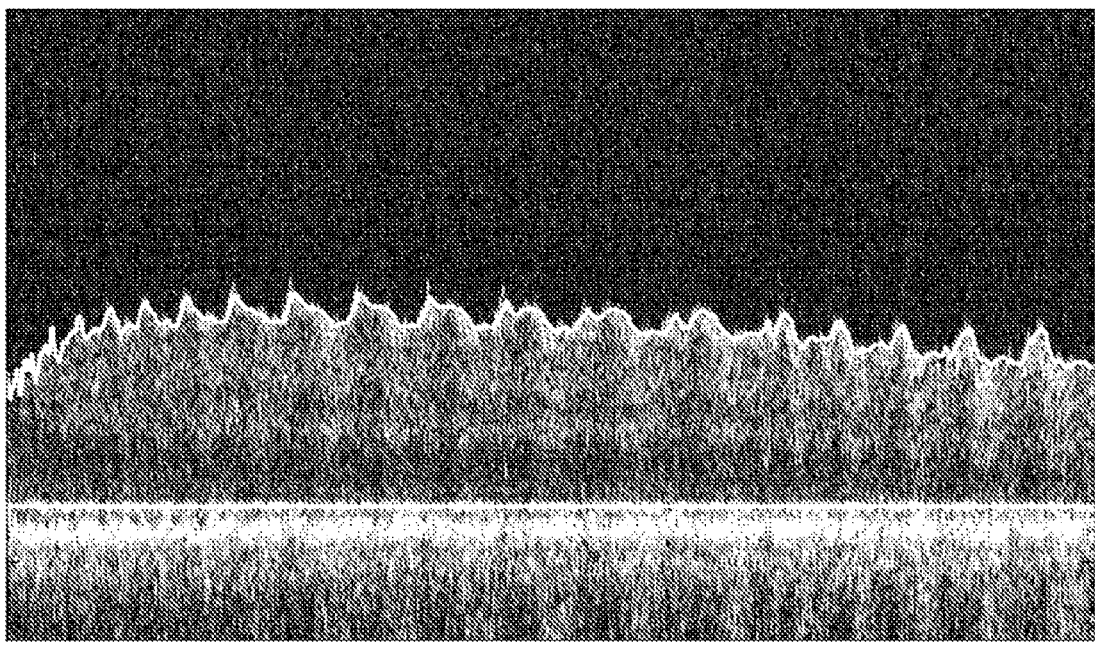
FIG. 4 shows a segmentation of grid optical coherence tomography image (displayed 2-dimensionally). Upper white line, inner retinal boundary; lower white line, inner segment/outer segment junction. The retinal thickness is defined as the distance between the 2 lines.
Figure 5:
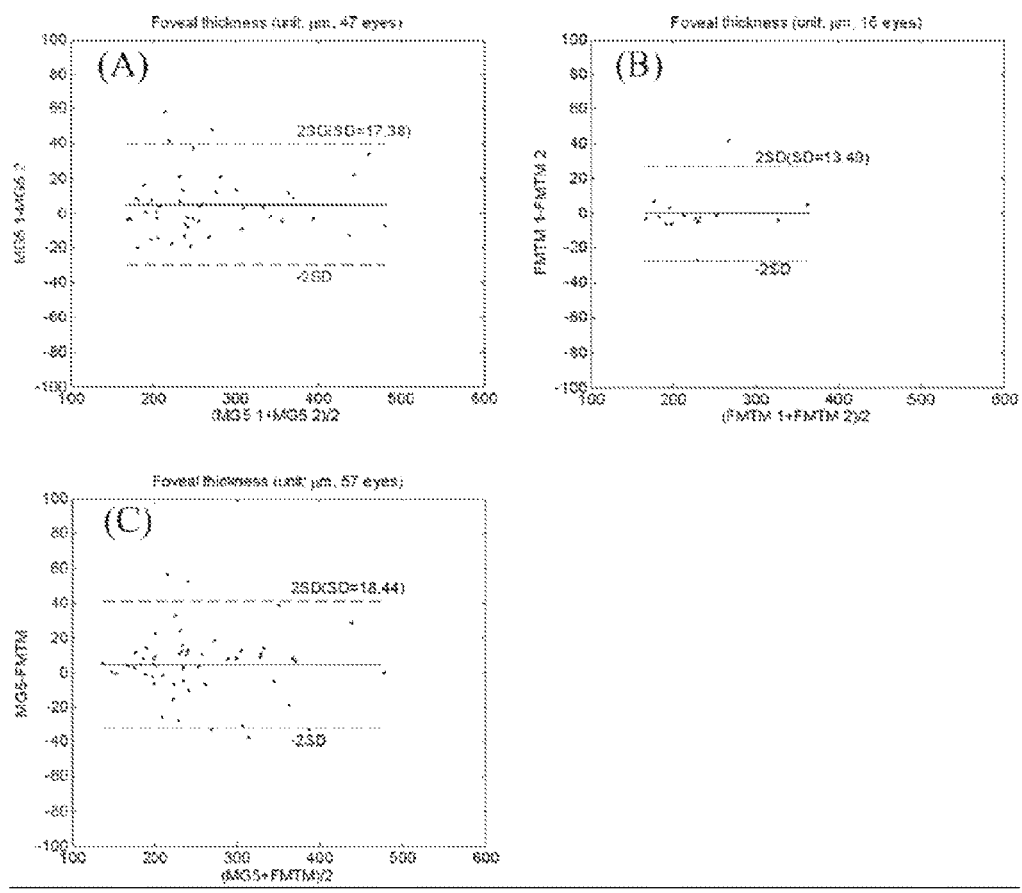
FIG. 5 shows a Bland-Altman plot of foveal thickness (area-weighted average in the central 1-mm-diameter circle). The solid line is the average difference (or agreement), and the dashed lines are the 95% limits of agreement. A, Comparison between 2 Macular Grid 5 (MG5) scans: average difference, 4.7 µm; standard deviation (SD) of difference, 17.4 µm. B, Comparison between 2 Fast Macular Thickness Map (FMTM) scans: average difference, 0.4 µm; SD difference, 13.5 µm. C, FMTM vs. MG5: average difference, 4.5 µm; SD difference, 18.4 µm.
Figure 6:
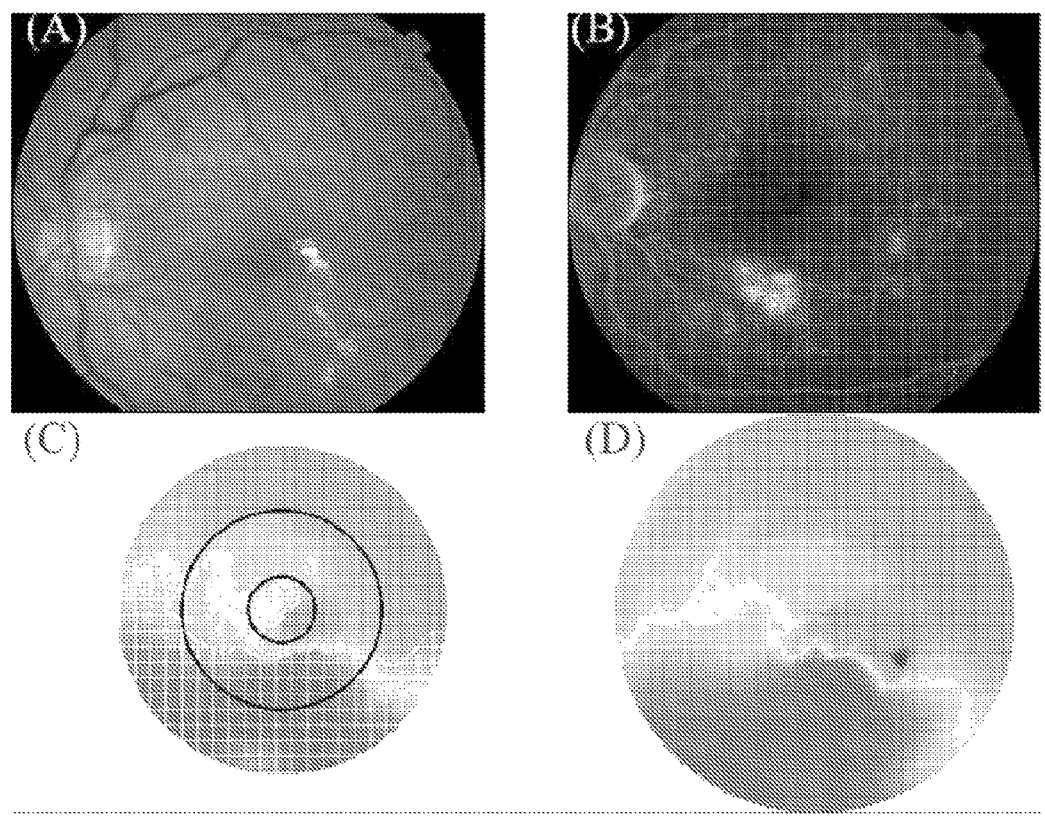
FIG. 6 shows images taken from cases of clinically significant macular edema (CSME) 1 and CSME 2 diagnosed by clinical examination (A, color fundus photograph; B, late fluorescein angiogram frame) and by Macular Grid 5 (C, MG5 thickness map) and Fast Macular Thickness Map (D, FMTM) protocols. The map of edema as identified by the MG5 algorithms is delineated by the white checkered zone in C.
Figure 7:
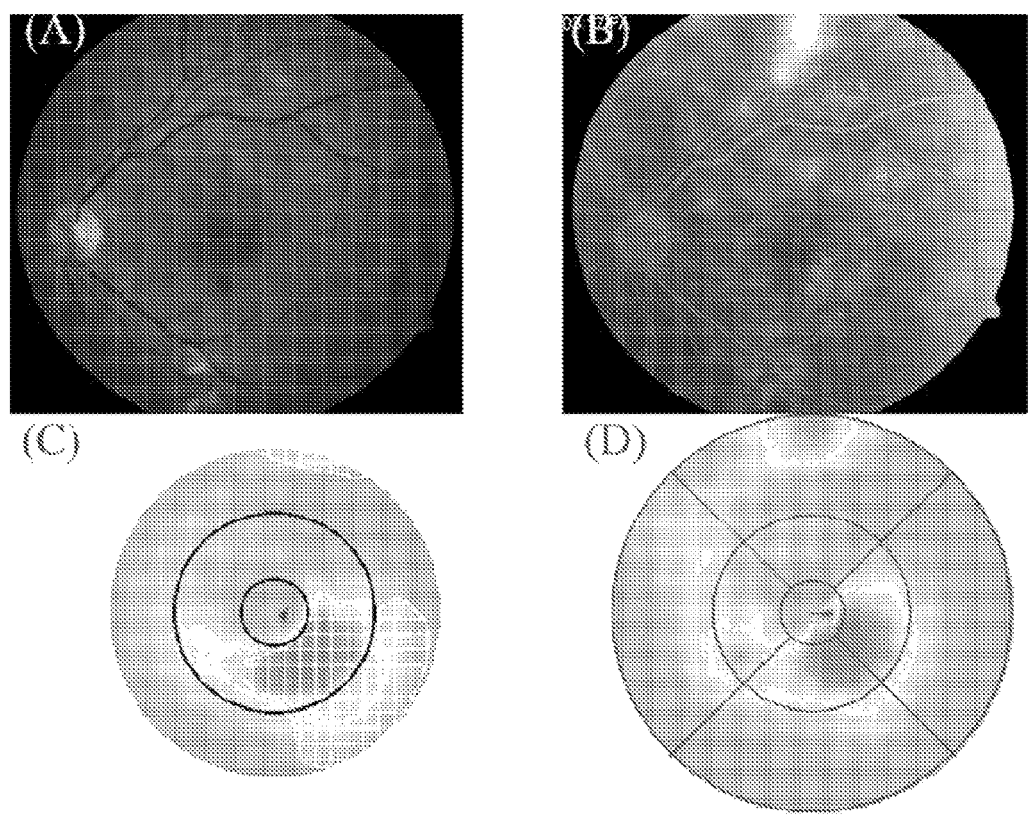
FIG. 7 shows images taken from cases of clinically significant macular edema (CSME) 2 but not CSME 1 diagnosed by clinical examination (A, color fundus photograph; B, late fluorescein angiogram frame) and by Macular Grid 5 (C, MG5 thickness map) and Fast Macular Thickness Map (D, FMTM) protocols. The map of edema as identified by the MG5 algorithms is delineated by the white checkered zone in C.

The automated detection of retinal boundaries was verified visually and found to be correct in 69 of 71 MG5 scans (our software) and on 65 of 71 FMTM scans (Stratus software). There was a trend for better reliability in automated segmentation by the MG5, but the difference was not statistically significant (X test, P=0.145). A total of 63 cases had both MG5 and FMTM with correct boundary detection, and constituted the case set used for subsequent analysis. FIG. 4 is an illustration of the accurate detection of inner and outer retinal boundaries by the MG5 analysis algorithm. Two MG5 scans were available for each eye. The repeatability (pooled SD) of the total area of edema was 0.48 mm$^2$ (coefficient of variation, 6.8%). Bland-Altman plots of the area-weighted average foveal thickness (diameter <1 mm) showed an average difference of 4.7 µm between the 2 MG5 scans (FIG. 5). To assess the accuracy of the MG5 relative to the existing OCT clinical practice standard, thickness maps were generated from both the FMTM and the MG5 analyses and compared. The thickness of the foveal region as measured by the FMTM and MG5 scans was substantially equivalent by Bland-Altman analysis (FIG. 5).

Comparison of the detection of macular edema by the MG5 versus the clinical assessment is shown in Table 1. Sensitivity and specificity of MG5 for detection of any CSME compared with the clinical examination (as the gold standard) were 89% (31/35) and 86% (24/28), respectively. Substantial (K >0.60) agreement (Table 1) was observed between the clinical assessment and the MG5 for the detection of CSME1, CSME2, and any CSME. The FMTM and MG5 also showed substantial agreement for the detection of CSME1 (Table 2).

The few cases that showed disagreement between the MG5 grade and the clinical assessment were rescrutinized to identify possible causes for disagreement. For cases in which the MG5 demonstrated CSME, cases diagnosed clinically with CSME showed a trend for a higher foveal thickness compared with cases where no CSME was evident clinically (Table 3). Cases without clinical CSME also tended to be farther from the foveal center. For cases in which MG5 did not identify CSME, the foveal thickness was slightly higher in cases clinically diagnosed with CSME compared with those without, though the difference was not statistically significant (Table 4).

Figure 8:
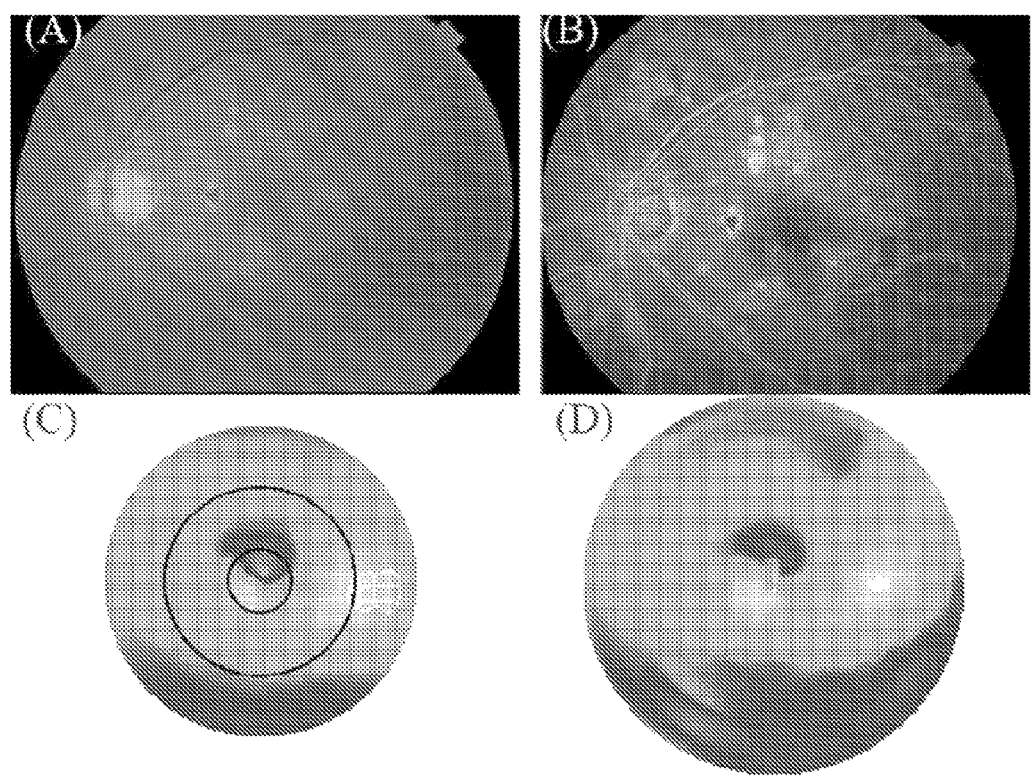
FIG. 8 shows images taken from patients diagnosed to have clinically significant macular edema (CSME) 1 by clinical examination (A, color fundus photograph; B, late fluorescein angiogram frame) but not by Macular Grid 5 (C, MG5 thickness map) or Fast Macular Thickness Map (D, FMTM) protocols. The map of edema as identified by the MG5 algorithms is delineated by the white checkered zone in C. Note that retinal thickening (compared with the normal reference) was present in the central circle of the MG5 map but did not meet the threshold level defined in this study.
Figure 9:
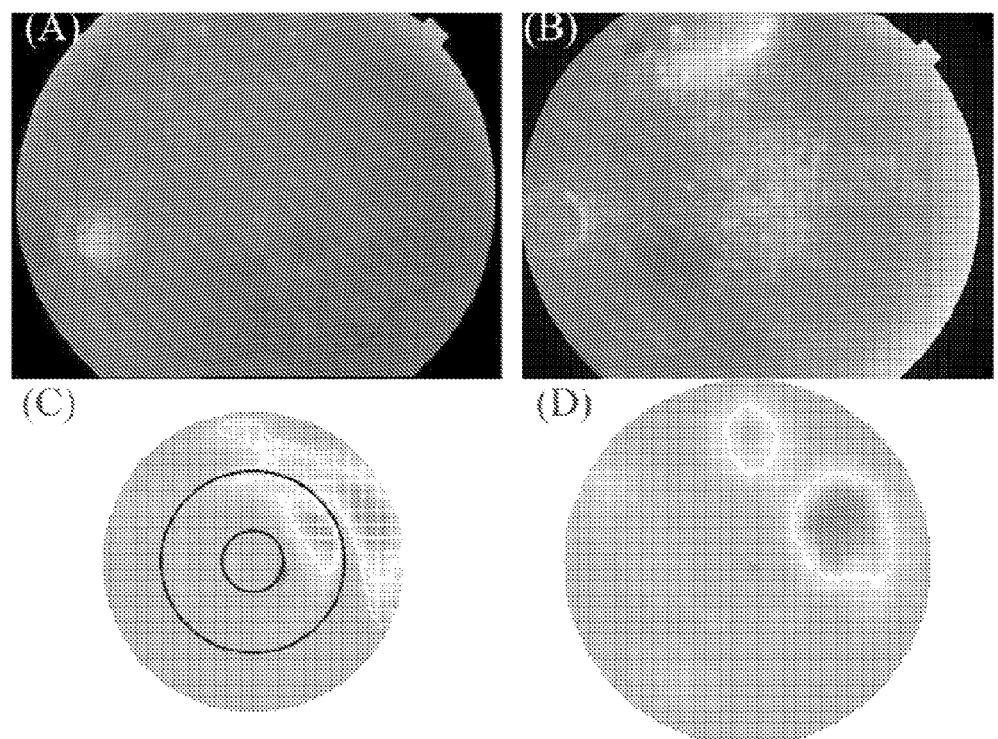
FIG. 9 shows images taken from cases graded to have clinically significant macular edema (CSME) 2 by Macular Grid 5 (MG5) but not identified by clinical examination. A, Color fundus photograph. B, Late fluorescein angiogram frame. C, Macular Grid 5 thickness map. D, Fast Macular Thickness Map (FMTM). The map of edema as identified by the MG5 algorithms is delineated by the white checkered zone in C. Note that the majority of the areas of retinal thickening were in the outer circle (i.e., >1 disk diameter from the foveal center). Note also the difference in configuration of the areas of retinal thickening in the outer circle between the MG5 map and the FMTM, which relies on more interpolation between data points in the outer zone.
Figure 10:
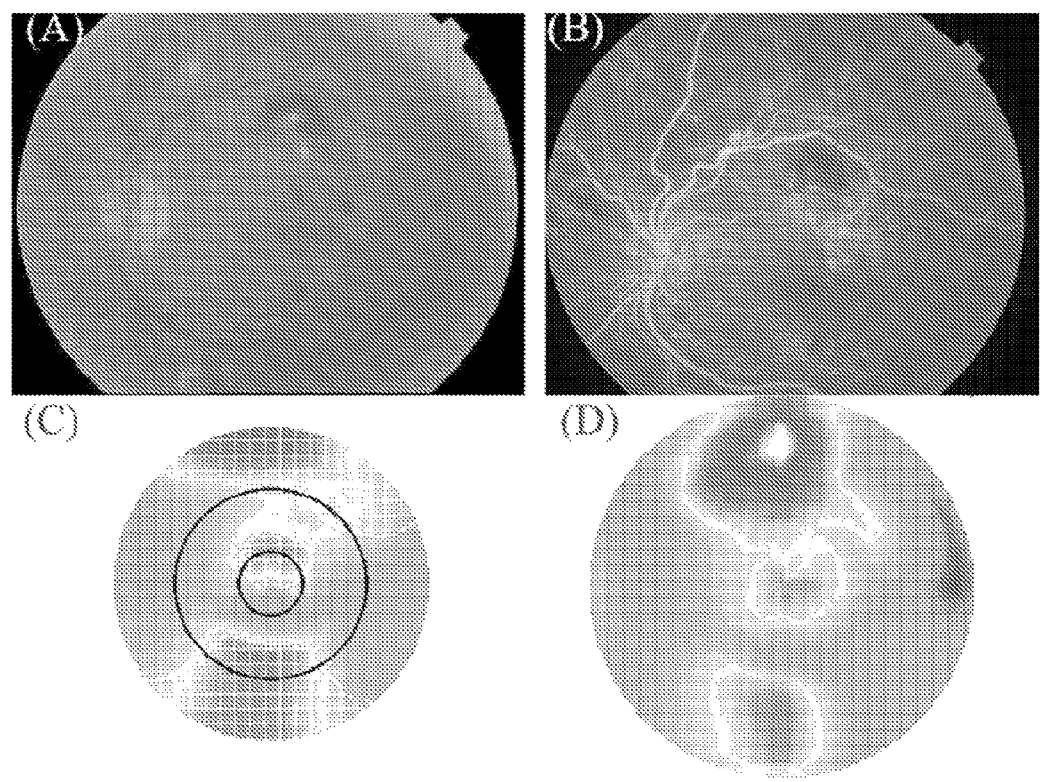
FIG. 10 shows images taken from cases graded to have clinically significant macular edema (CSME) 1 by Macular Grid 5 (MG5) and Fast Macular Thickness Map (FMTM) but not identified by clinical examination. A, Color fundus photograph. B, Late fluorescein angiogram frame. C, Macular Grid 5 thickness map. D, FMTM. The map of edema as identified by the MG5 algorithms is delineated by the white checkered zone in C. Note that the retinal thickening inside the central foveal circle is above threshold on the MG5 map, but not as severe as the area of edema just outside the circle. This may explain why the clinician did not judge the edema to be within the foveal zone.

Representative cases of agreement and disagreement between the MG5 and the clinical assessment are shown in FIGS. 6, 7, and 8 to 10. The disagreements seemed to be due to a threshold phenomenon in which retinal thickening (above the normal baseline) was apparent on the MG5 map but did not achieve the MG5 threshold definition for edema (FIG. 8). In cases such as this, the clinician may have been influenced by other factors, such as the presence of lipid exudates, which may have led the clinician to adopt a lower threshold for thickening. Alternatively, the retinal thickening identified by the MG5 was just close enough to the foveal center to be considered clinically significant by the MG5 algorithm, but was deemed to be farther away by the clinician, who may not have been able to measure the distance to the foveal center as precisely (FIG. 9). In other cases, the clinician may have been biased by the presence of prominent or severe thickening in one region and, as a result, may have been less impressed by or less sensitive to retinal thickening in adjacent areas (FIG. 10).

The minimum distance between the foveal center and the edge of the MG5-identified area of edema was compared with the measured logarithm of the minimum angle of resolution visual acuity at the time of assessment. For cases in which the edema extended into the foveal center, the distance was expressed as a negative value, indicating the minimum distance to nonedematous retina. No significant correlation between acuity and distance to edema edge was observed (data not shown).

Discussion

In the above examples, we described a new macular grid scan pattern (MG5) for the Stratus OCT that provides a more evenly sampled map of the macula compared with standard radial line and fast macular thickness (FMTM) protocols commonly used by clinicians in practice for the quantification of DME. The sampling gap in the FMTM steadily rises with increasing eccentricity (FIG. 2), with a gap between points that can be 5-fold greater than the MG5 at a distance of 2.5 mm from the foveal center. The large gaps (up to 1.6 mm) in the FMTM are of particular problem when considering the assessment of CSME, which, in some cases, may not extend closer than 1 mm from the foveal center.

In this analysis, the processing program used to generate thickness measurements and assessments of edema from the MG5 scan is demonstrated to be both accurate and repeatable for any given subject. The average difference between area weighted average thickness was only 4.5 µm between FMTM and MG5 scans, and was only 4.7 µm between the 2 MG5 scans. Moreover, the coefficient of variation in the area of macular edema between repeat scans in this series was only 6.8%.

Reproducibility of OCT thickness measurements is of paramount importance in clinical trials and in monitoring the response of patients to therapy in clinical practice. Excellent reproducibility of thickness measurements has been demonstrated in normal subjects, with a repeatability coefficient of <7 µm in one study and an intervisit SD of only 2.4 µm in another series. In Massin et als study [5] the repeatability coefficient for patients with DME was worse but still reasonably good, measuring <21 µm, in all but 1 of 10 patients. The improved repeatability of the total macular volume is likely due to the larger area sampled by the parameter, thereby rendering the measure less sensitive to fixation errors. The downside of using the total macular volume for clinical trials, however, is that it may also be less sensitive for detecting changes in edema if the area of edema is small relative to the area of the entire macula. The development of algorithms to identify the area (or volume) of edema, as described in this invention, addresses these limitations. Because an area (or volume) is measured, rather than the thickness at a single point (such as the foveal center), the parameter also will be less sensitive to fixation errors as long as the edematous region remains within the scanned zone. At the same time, because only the edematous region is measured, the method will retain its sensitivity to detect changes in the edema. This retinal edema area or volume is a valuable parameter for clinicians in following their patients' response to therapy, and the edema maps (see checkered outline in FIGS. 6, 7 and 8-10) produced by the MG5 grid analysis provide the clinician with a quick and tangible snapshot of the patient's retinal status.

If scanned data are to be used to quantify retinal edema, the use of a scanning pattern, such as the MG5, that provides a more uniform or evenly spaced sampling of the macula would seem to be preferred. In the examples provided herein, MG5 types of scanning pattern demonstrated good agreement with the clinical examination for the detection of CSME. The MG5 assessment of CSME 1 also showed good agreement with the FMTM. The agreement for identification of CSME 2 by the MG5 seemed to be better than that for CSME 1, possibly reflecting the improved sampling in the outer zones of the grid. It is important to note that the thresholds for identifying edematous areas (99%-99.5% confidence interval relative to the reference mean) were judiciously chosen in an attempt to achieve reasonable sensitivity without a severe penalty in loss of specificity. Furthermore, this standard MG5 threshold was applied consistently to all cases, in contrast to the subjective clinician assessments, which may have varied due to the assessment method used by the grader (e.g., contact lens vs.

90-diopter lens examination) or the level of stereopsis available in the fundus photographs. This variability in the clinical assessment may explain the few cases of disagreement observed in this study (some examples illustrated in FIGS. 8-10). Review of all of these cases of disagreement suggested that assessments by clinicians could be biased by context. For example, the presence of lipid exudates seemed to increase the clinician's sensitivity for identifying retinal thickening. Although this may have been an attempt by the clinician to identify the third ETDRS category of CSME (lipid within 500 μm of the foveal center with adjacent thickening), this was not supported by the OCT maps, which did not appear to show more marked retinal thickening in areas adjacent to the lipid. These observations are consistent with the mean foveal thickness measurements in Table 4, which suggest that, in some cases, clinicians can identify edema that is recognizable on the OCT map but is below the arbitrary threshold chosen in this study. On the other hand, the presence of severe thickening in some areas seemed to reduce the clinician's sensitivity for detecting milder (though well above the MG5 threshold) degrees of thickening in adjacent or contiguous regions (FIG. 10, Table 3). These cases and the mean thickness measurements shown in Tables 3 and 4 highlight the variability and subjectivity of clinical assessments and the apparent value of the objective and reproducible threshold utilized by the MG5 analysis, particularly in cases of borderline CSME.

Another significant limitation of the study is its retrospective design. Although the photography protocol used in the imaging unit was well standardized and consistently applied, there may be some variability in quality of the clinician's assessment of macular edema as a result of the retrospective nature of the study. Clinicians judged edema based on their prior training and experience. No protocol or specialized training was provided to clinicians to standardize their recognition and diagnosis of areas of retinal edema. In addition, in some cases stereoscopic photographs were used to assist in classifying the edema. These limitations may account for the variability in clinician assessment of edema observed in this study. Thus, performance of methods of the present invention may potentially be even better than what has been demonstrated in the examples here.

The additional information (by improved sampling) from the perifoveal macula provided by the MG5 may be of value in future clinical studies and in monitoring the response of nonfoveal edema to intervention. The MG5 data also can be used to generate other potentially useful parameters such as the distance between the edema and the foveal center. In addition, the ability of these algorithms to detect macular edema automatically and objectively may assist clinicians in identifying patients requiring treatment. The maps of the areas of retinal thickening also may be of value in planning the location and extent of focal laser treatment. Moreover, automated detection of CSME by OCT MG5 may be of value in screening programs aimed at identifying patients with sight-threatening retinopathy.

Automated classification using the MG5 scan pattern in this study generally correlated well with clinical grading and standard OCT analysis (FMTM). It is important to note that MG5 algorithms were designed to detect CSME and not subclinical macular edema evident only on OCT. MG5 provides considerably more information in the perifoveal macula than FMTM and may facilitate the diagnosis and monitoring of nonfoveal CMSE. Automated grading improves the objectivity, reproducibility, sensitivity, and precision of CSME diagnosis and is a useful tool both in clinical studies and in clinical practice.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

TABLE 1

| | MG5 vs. Clinical Examination* | | | |
|---|---|---|---|---|
| | CSME 1 | CSME 2 | Any CSME† | Any DME‡ |
| Edema present on MG5 only | 7 | 5 | 4 | 7 |
| Edema present on clinical examination only | 3 | 3 | 4 | 4 |
| Both | 22 | 25 | 31 | 37 |
| None | 31 | 30 | 24 | 15 |
| κ (95% CI) | 0.677 (0.495-0.860) | 0.745 (0.580-0.910) | 0.743 (0.577-0.909) | 0.603 (0.393-0.814) |
| Agreement | 0.841 | 0.873 | 0.873 | 0.825 |
| Sensitivity (95% CI) | 0.880 (0.677-0.968) | 0.893 (0.706-0.972) | 0.866 (0.723-0.963) | 0.902 (0.759-0.968) |
| Specificity (95% CI) | 0.816 (0.651-0.9168) | 0.857 (0.690-0.946) | 0.857 (0.664-0.953) | 0.682 (0.451-0.853) |

CI = confidence interval;
CSME 1 = any retinal thickening within 500 μm of the foveal center;
CSME 2 = retinal thickening within 1 Macular Photocoagulation Study (MPS) disc diameter (1.5 mm) of the foveal center and >1 MPS disc area in size. Sensitivity and specificity for MG5 are calculated with respect to the clinical gold standard.
*Grading as assessed by biomicroscopy and/or stereo photography.
†CSME 1 or 2 of lipid within 500 μm of the foveal center associated with adjacent retinal thickening.
‡Presence of any retinal thickening within the macula.

TABLE 2

| Grading Methods Compared | FMTM vs. Clinical Examination‡ | FMTM vs. MG5 |
|---|---|---|
| CSME 1 present on FMTM only | 4 | 2 |
| CSME 1 present on clinical examination or MG5 only | 6 | 8 |
| CSME 1 present on both FMTM and clinical examination or MG5 | 19 | 21 |
| None | 34 | 32 |
| κ (95% CI) | 0.664 (0.474-0.854) | 0.676 (0.492-0.860) |
| Agreement | 0.841 | 0.841 |
| Sensitivity (95% CI) | 0.760 (0.545-0.898) | 0.724 (0.525-0.866) |
| Specificity (95% CI) | 0.895 (0.743-0.966) | 0.941 (0.789-0.990) |

CI = confidence interval;
MG5 = Macular Grid 5 analysis.
Sensitivities and specificities for the FMTM are calculated with respect to either the clinical examination or the MG5 assessment as the gold standard.
*Any retinal thickening within 500 μm of the foveal center.
†Evaluation of foveal subfield only.
‡Grading as assessed by biomicroscopy and/or stereo photography.

TABLE 3

|  | Clinical CSME+ | Clinical CSME− | P Value |
|---|---|---|---|
| Mean distance to fixation* (±SD) (mm) | −0.16 (0.67) | 0.47 (0.63) | 0.14 |
| Mean edema area (±SD) (mm)$^2$ | 8.63 (5.79) | 8.41 (3.04) | 0.91 |
| Mean foveal thickness† (±SD) (μm) | 317 (77) | 251 (47) | 0.06 |

SD = standard deviation.
+, present by clinical grading;
−, absent by clinical grading,
*The minimum distance from edema edge to foveal center. If edema extends through the foveal center, the distance measurement will have a negative value (indicating the minimum distance from the foveal center to nonedematous retina).
†Average retinal thickness in the fovea (diameter <1 mm).

TABLE 4

|  | Clinical CSME+ | Clinical CSME− | P Value |
|---|---|---|---|
| Mean distance to fixation* (±SD) | 2.09 (0.53) | 2.26 (0.45) | 0.57 |
| Mean edema area (±SD) | 0.36 (0.46) | 0.32 (0.65) | 0.90 |
| Mean foveal thickness† (±SD) | 221 (42) | 204 (31) | 0.50 |

SD = standard deviation.
+, present by clinical grading;
−, absent by clinical grading.
*The minimum distance from edema edge to foveal center. If edema extends through the foveal center, the distance measurement will have a negative value (indicating the minimum distance from the foveal center to nonedematous retina),
†Average retinal thickness in fovea (diameter <1 mm).

REFERENCES

[1] Early Treatment Diabetic Retinopathy Study Research Group. Treatment techniques and clinical guidelines for photocoagulation of diabetic macular edema. Early Treatment Diabetic Retinopathy Study report number 2. Ophthalmology 1987; 94: 761-74.

[2] Brown J C, Solomon S D, Bressler S B, et al. Detection of diabetic foveal edema: contact lens biomicroscopy compared with optical coherence tomography. Arch Ophthalmol 2004; 122:330-5.

[3] Cohen J. A coefficient of agreement for nominal scales. Educ Psychol Meas 1960; 20:37-46.

[4] Landis J R, Koch G G. The measurement of observer agreement for categorical data. Biometrics 1977; 33:159-74.

[5] Massin P, Vicaut E, Haouchine B, et al. Reproducibility of retinal mapping using optical coherence tomography. Arch Ophthalmol 2001; 119:1135-42.

[6] Paunescu L A, Schuman J S, Price L L, et al. Reproducibility of nerve fiber thickness, macular thickness, and optic nerve head measurements using Stratus OCT. Invest Ophthalmol Vis Sci 2004; 45:1716-24.

What is claimed is:

1. A computer implemented system for identifying regions of macular edema in a subject, comprising:
   an input unit adapted for receiving an input retinal thickness map generated by an optical coherence tomography device; and
   a processing unit configured to perform a method for analyzing the retinal thickness map, comprising the steps of:
       comparing the input retinal thickness map with a normal reference map to identify regions of abnormal retinal thickness in the macular region,
       wherein the normal reference map is compiled from retinal thickness maps of a population with normal eyes, and wherein a point on the input retinal thickness map is abnormal if it meets predetermined comparison criteria,
   whereby a region of macular edema is identified based on comparisons of the retinal thickness maps.

2. The system of claim 1, wherein the normal reference map is stored on an internal storage of the system.

3. The system of claim 1, wherein the normal reference map is stored on a remote central database.

4. The computer implemented system of claim 1, wherein said input retinal thickness map is generated by an optical coherence tomography device employing a scanning pattern comprising a plurality of evenly spaced axial scans forming a circular grid.

5. The computer implemented system of claim 1, wherein said normal reference map is compiled from retinal thickness maps of a population with normal eyes, and said normal reference map comprises a mean value map and a standard deviation map.

6. The computer implemented system of claim 5, wherein said predetermined criteria are based on the mean value map and standard deviation map of the normal reference map.

7. The computer implemented system of claim 1, wherein said processing unit is configured to perform a further step of identifying an edema kernel by finding one or more locations on the input retinal thickness map where the value is greater than a predetermined standard deviation above the mean value at the same location of the normal reference map.

8. The computer implemented system of claim 7, wherein said edema kernel are locations having values greater than 2.33 standard deviation above a normal reference mean at the corresponding location of the reference map.

9. The computer implemented system of claim 7, wherein said processing unit is configured to perform the further step of identifying zones of edema by expanding a region of edema via assessing the thickness of locations neighboring an edema kernel and adding the locations to the region if it has a thickness greater than a predetermined thickness.

* * * * *